(12) United States Patent
Cleary (10) Patent No.: US 9,498,304 B2
(45) Date of Patent: *Nov. 22, 2016

(54) ORTHODONTIC ATTACHMENT MODULE FOR INTRA-ORAL BITE CORRECTORS

(71) Applicant: 3M INNOVATIVE PROPERTIES COMPANY, St. Paul, MN (US)

(72) Inventor: James D. Cleary, Glendora, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 14/221,072

(22) Filed: Mar. 20, 2014

(65) Prior Publication Data

US 2014/0205963 A1    Jul. 24, 2014

Related U.S. Application Data

(63) Continuation of application No. 12/144,728, filed on Jun. 24, 2008, now Pat. No. 8,714,974, which is a continuation-in-part of application No. 11/831,445, filed on Jul. 31, 2007, now abandoned.

(51) Int. Cl.
*A61C 7/36* (2006.01)
*A61C 7/12* (2006.01)
*A61C 7/28* (2006.01)

(52) U.S. Cl.
CPC . *A61C 7/36* (2013.01); *A61C 7/12* (2013.01); *A61C 7/282* (2013.01)

(58) Field of Classification Search
CPC ........... A61C 7/28; A61C 7/282; A61C 7/36
See application file for complete search history.

(56) References Cited

U.S. PATENT DOCUMENTS

| | | |
|---|---|---|
| 3,798,773 A | 3/1974 | Northcutt |
| 4,127,940 A | 12/1978 | Shilliday |
| 4,226,589 A | 10/1980 | Klein |
| 4,368,039 A | 1/1983 | Armstrong |
| 4,382,783 A | 5/1983 | Rosenberg |
| 4,406,620 A | 9/1983 | Kaprelian et al. |
| 4,462,800 A | 7/1984 | Jones |
| 4,472,138 A | 9/1984 | Howe |
| 4,496,318 A | 1/1985 | Connelly |
| 4,551,095 A | 11/1985 | Mason |
| 4,553,934 A | 11/1985 | Armstrong et al. |
| 4,708,646 A | 11/1987 | Jasper |
| 5,352,116 A | 10/1994 | West |
| 5,374,187 A | 12/1994 | Vashi |
| 5,435,721 A | 7/1995 | Vogt |
| 5,562,445 A | 10/1996 | DeVincenzo et al. |
| 5,645,423 A | 7/1997 | Collins, Jr. |
| 5,645,424 A | 7/1997 | Collins, Jr. |
| 5,651,672 A | 7/1997 | Cleary et al. |

(Continued)

OTHER PUBLICATIONS

International Search Report for PCT/US2008/069578, prepared by the European Patent Office, mailed Oct. 7, 2008.

(Continued)

*Primary Examiner* — Ralph Lewis (57) ABSTRACT

A module for attaching an orthodontic bite corrector to an orthodontic buccal tube appliance includes two segments, and each segment includes a rotation stop for limiting undesired rotational movement of bite corrector during movement of the patient's jaws. The segments are movable relative to each other during installation of the attachment module for facilitating placement of the rotation stops in regions next to the buccal tube appliance that might otherwise be difficult to access.

21 Claims, 6 Drawing Sheets

(56) References Cited

U.S. PATENT DOCUMENTS

| | | |
|---|---|---|
| 5,678,990 A | 10/1997 | Rosenberg |
| 5,695,332 A * | 12/1997 | Samuels .................. A61C 7/06 433/5 |
| 5,711,667 A | 1/1998 | Vogt |
| 5,964,588 A | 10/1999 | Cleary |
| 5,980,247 A | 11/1999 | Cleary |
| 6,053,730 A | 4/2000 | Cleary |
| 6,120,289 A | 9/2000 | Cleary et al. |
| 6,234,791 B1 | 5/2001 | Cleary |
| 6,325,622 B1 | 12/2001 | Kelly et al. |
| 6,558,160 B2 | 5/2003 | Schnaitter |
| 6,669,474 B2 | 12/2003 | Vogt |
| 6,913,460 B2 | 7/2005 | Cleary |
| 8,714,974 B2 * | 5/2014 | Cleary .................... A61C 7/12 433/17 |
| 2003/0175651 A1 | 9/2003 | Dinkelis |
| 2006/0046224 A1 | 3/2006 | Sondhi |

OTHER PUBLICATIONS

Forsus brand Fatigue Resistant Device EZ Module Data Sheet; 3M Unitek, Monrovia, CA © 2006, 2 pages.
Forsus Fatigue Resistant Device EZ Module—Installation Guide; 3M Unitek, Monrovia, CA; © 2006, 2 pages.

* cited by examiner

ORTHODONTIC ATTACHMENT MODULE FOR INTRA-ORAL BITE CORRECTORS

CROSS-REFERENCE TO RELATED APPLICATIONS

This application is a continuation of U.S. application Ser. No. 12/144,728, filed Jun. 24, 2008, which is a continuation-in-part application of U.S. application Ser. No. 11/831,445, filed Jul. 31, 2007.

BACKGROUND OF THE INVENTION

1. Field of the Invention

This invention relates to an attachment module used in the course of orthodontic treatment. More particularly, the present invention is directed to an attachment module for connecting bite correctors, force modules or other devices to other orthodontic components in the oral cavity.

2. Description of the Related Art

Orthodontic treatment is a specialized form of treatment within the field of dentistry, and involves movement of malpositioned teeth to orthodontically correct locations. Orthodontic treatment often greatly improves the aesthetic appearance of the patient's teeth. Orthodontic treatment can also improve the patient's occlusion, so that when the jaws are closed the upper teeth are in proper positions relative to the lower teeth.

Orthodontic treatment is often carried out by use of a system of tiny appliances, wires and other components that are commonly known collectively as "braces". Typically, a small appliance known as a bracket is connected to each of the patient's anterior, cuspid and bicuspid teeth and an archwire placed in a slot of each bracket. The archwire forms a track to guide movement of the brackets and the associated teeth to desired positions.

End sections of orthodontic archwires are often held by appliances known as buccal tubes that are secured to the patient's molar teeth. Each buccal tube has a passage that slidably receives the end section of the archwire. Buccal tubes may be placed on the patient's first molar teeth or the patient's second molar teeth.

In orthodontic treatment, the molar teeth often serve as convenient points of anchorage for applying force to other teeth because the molar teeth are relatively large and have a plurality of roots. As a consequence, many buccal tube appliances have one or two additional passages located next to the archwire slot. The additional passages (sometimes called auxiliary tubes) can be used for connection to other orthodontic devices as desired.

For example, the orthodontic treatment of some patients includes correction of the alignment of the upper dental arch to the lower dental arch. Certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

A number of intra-oral devices for correcting Class II and Class III malocclusions are known in the art. For example, U.S. Pat. Nos. 4,708,646, 5,352,116, 5,435,721 and 5,651,672 describe intra-oral bite correctors with flexible spring members that are connected to upper and lower arches of a patient. The length of the bite corrector is selected such that the member is curved in an arc when the patient's jaws are closed. The inherent spring bias tends to urge the members toward a normally straight orientation and provide a force that pushes one dental arch forward or rearward relative to the other dental arch when the jaws are closed.

U.S. Pat. No. 6,913,460 describes an orthodontic coupling for releasably connecting intra-oral bite correctors to buccal tubes. The coupling described in this patent includes a body with a shank that is received in a passage of the buccal tube with a flexible, snap-in retention movement. In certain embodiments described in this patent, the coupling includes rotation stops that are moved into operative positions as the shank is received in the passage. The rotation stops function to limit pivoting movement of the associated bite corrector so that the bite corrector does not contact adjacent oral tissue and cause irritation.

Relatively large intra-oral forces are often applied to orthodontic components during movement of the jaws. For example, the forces generated when chewing can be significant, especially when the patient bites into a hard food object such as hard candy, nuts or ice. The chewing forces can be especially large in molar regions of the patient's jaws, and hard food objects can transmit the forces to the attached orthodontic components. In some instances, the forces can break the components or cause the components to spontaneously detach from the teeth such that the progress of treatment is interrupted.

SUMMARY OF THE INVENTION

The present invention is directed toward an improved attachment module for an orthodontic bite corrector, along with related orthodontic assemblies and methods. The attachment module comprises two segments, and each segment includes a rotation stop. The segments are movable relative to each other in order to facilitate placing both rotation stops in beneficial operative positions that help limit undue rotational movements of associated orthodontic components.

In more detail, the present invention in one aspect is directed toward an orthodontic attachment module for an orthodontic bite corrector. The attachment module comprises a first segment including an elongated shank for reception into a passage of an orthodontic buccal tube appliance. The first segment also includes a first rotation stop that is spaced from the shank in a direction along a first reference axis. The first rotation stop extends in a direction generally parallel to the shank. The attachment module also comprises a second segment that includes a coupling for connection to an orthodontic bite corrector. The second segment also includes a second rotation stop. The second segment is movable relative to the first segment between an open orientation and a closed orientation. The second rotation stop is spaced from the shank in a direction along a second reference axis that is generally perpendicular to the first reference axis.

Another aspect of the present invention is directed toward an orthodontic assembly that comprises a buccal tube appliance including a base and a body extending outwardly from the base. The body includes first wall portions defining an archwire slot extending in a generally mesial-distal direction and second wall portions defining a passage extending in a generally mesial-distal direction. The assembly also comprises an attachment module that is releasably connected to the buccal tube appliance. The attachment module includes a shank extending into the passage and a first rotation stop extending over the body. The first rotation stop is located in a facial direction relative to at least a portion of the body. The attachment module also includes a second rotation stop extending along the second wall portions and located in a lingual direction relative to the passage. The second rotation stop is movable relative to the first rotation stop.

Another aspect of the present invention is directed toward a method of coupling an orthodontic attachment module to an orthodontic buccal tube appliance. The method comprises:

providing a buccal tube appliance having first wall portions defining an elongated archwire slot and second wall portions defining an elongated passage extending alongside the archwire slot;

placing a shank of an attachment module in the passage; and moving a rotation stop of the attachment module into a region that is located in a lingual direction relative to the second wall portions, and wherein the act of moving the rotation stop into the region is carried out at a time other than during the act of placing the shank in the passage.

The attachment module of the present invention provides a secure and robust connection between the buccal tube appliance and a bite corrector, force module or other intra-oral component. The movable relationship of the first rotation stop to the second rotation stop helps enable the rotation stops to be securely coupled to the buccal tube appliance in a manner that might otherwise be difficult or impossible to attain. As a result, the orthodontic components such as a bite corrector associated with the attachment module can better resist undue forces from jaw movement that may be encountered during the course of treatment.

These and other aspects of the invention are described in more detail in the paragraphs that follow and are illustrated in the accompanying drawings.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

Figure 1:
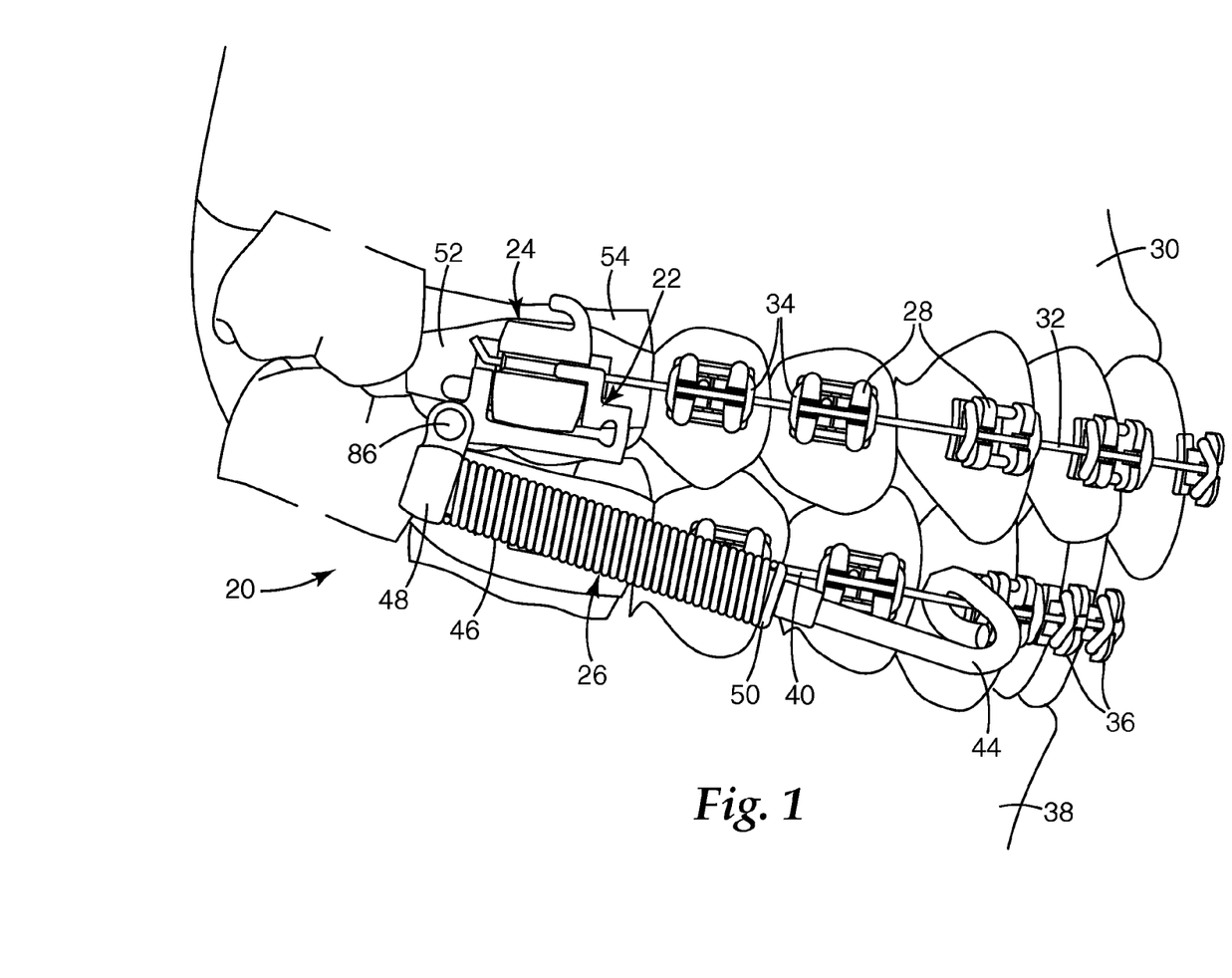
FIG. 1 is a fragmentary side elevational view showing an example of a patient undergoing orthodontic treatment, wherein an attachment module of the present invention is used to connect a bite corrector to a buccal tube appliance that is mounted on the patient's upper right first molar tooth.

An orthodontic assembly according to one embodiment of the present invention is illustrated in FIG. 1 and is broadly designated by the numeral 20. The assembly 20 includes an attachment module 22, a buccal tube appliance 24 and a bite corrector 26. The assembly 20 is connected to other components of an orthodontic brace that is worn by a patient undergoing orthodontic treatment.

In FIG. 1, a number of slotted orthodontic brackets 28 are fixed to the teeth of the patient's upper jaw 30 and an archwire 32 is received in the archwire slot of each bracket 28. An elastomeric O-ring ligature 34 extends around tiewings of each bracket 28 in order to retain the archwire 32 in the archwire slots of the brackets 28.

Similarly, a number of slotted orthodontic brackets 36 are fixed to the teeth of the patient's lower jaw 38. An archwire 40 is received in the slot of each bracket 36. An elastomeric O-ring ligature extends around the tiewings of each bracket 36 in order to retain the archwire 40 in the archwire slots of the brackets 36.

The right distal end of the upper archwire 32 is received in an archwire slot 60 (FIGS. 2-3 and 5) of the buccal tube appliance 24. Optionally, an end section of the archwire 32 is bent as shown in FIG. 1 in a location adjacent the distal side of the buccal tube appliance 24.

The bite corrector 26 is preferably similar to the bite corrector described in U.S. Pat. No. 5,964,588. In brief, the bite corrector 26 includes a first elongated tubular member, a second elongated tubular member that is received in the first member in sliding, telescoping relation, and a third member 44 that is received in the second member. A helical compression spring 46 extends around the first tubular member and has an outer end that bears against a connector 48 of the bite corrector 26 that is fixed to the first member. The opposite end of the spring 46 bears against an annular fitting 50 that is secured to an outer end section of the second member.

Preferably, the outer end of the third member 44 is formed into a loop-type configuration as shown in FIG. 1 that extends around a section of the lower archwire 40. Additional examples of suitable loop-type configurations are set out in U.S. Pat. No. 6,669,474 (Vogt). The outer end of the third member 44 also preferably includes a line of weakness such as a recess or other area of reduced thickness for ease of bending the outer end section around the lower archwire 40. Examples of suitable commercially-available bite correctors 26 include "Forsus" brand fatigue resistant Class II correctors from 3M Unitek Corporation.

Preferably, the overall effective length of the bite corrector 26 is selected so that the first and second members are not fully compressed and the second member is not fully inserted into the first member when the patient's jaws 30, 38 are closed. As a consequence, the inherent bias of the spring 46 provides the desired corrective forces by urging the first and second member away from each other in order to move one dental arch relative to the other.

The buccal tube appliance 24 is shown in enlarged view in FIGS. 2-5 and includes a base 50. In the illustrated example, the base 50 is affixed to a band 52 that is depicted in FIG. 1. The band 52 encircles the patient's upper right first molar tooth 54 and is connected to the buccal tube appliance 24 by a weld or a braze joint. Optionally, the buccal tube appliance 24 may be connected to the molar tooth 54 by other means such as an adhesive bond between the base 50 and the enamel surface of the molar tooth 54, although use of the band 52 as illustrated is often preferred.

The buccal tube appliance 24 has a body 56 that extends outwardly from the base 50 in a generally facial direction. The body 56 includes first wall portions 58 adjacent the archwire slot 60. In the illustrated embodiment, the first wall portions 58 include parallel, spaced-apart occlusal and gingival inner flat wall surfaces and an inner flat lingual wall surface that is perpendicular to the occlusal and gingival wall surfaces. The inner surfaces of the first wall portions 58 present a generally "U"-shaped configuration in transverse view and define the archwire slot 60.

The buccal tube appliance 24 also includes a cap 62 that extends across the archwire slot 60 and is detachably connected to the first wall portions 58. The cap 62 can be removed if desired to open the archwire slot 60 during a later stage of orthodontic treatment, such as a point in time after the second molar tooth of an adolescent patient has sufficiently erupted. Once the cap 62 is removed, the archwire slot 60 functions in a manner similar to the archwire slots of the orthodontic brackets 28, 36.

The body 56 of the buccal tube appliance 24 also includes second wall portions 64 that extend next to a passage 66. Both the archwire slot 60 and the passage 66 extend in generally mesial-distal directions, although the passage 66 may not extend in a direction that is precisely parallel to the direction of extension of the archwire slot 60. For example, the archwire slot 60 may be inclined relative to the base 50 of the buccal tube appliance 24 in order to apply forces to the adjacent teeth in certain inclined directions or along rotational paths.

Figure 2:
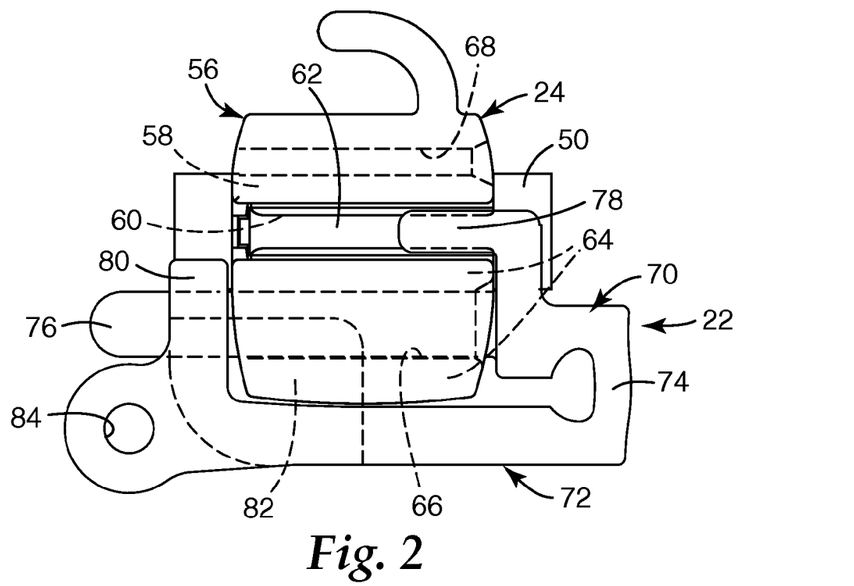
FIG. 2 is an enlarged front elevational view of the attachment module and buccal tube appliance alone that are depicted in FIG. 1, looking at the attachment module and the buccal tube appliance in a lingual direction.
Figure 3:
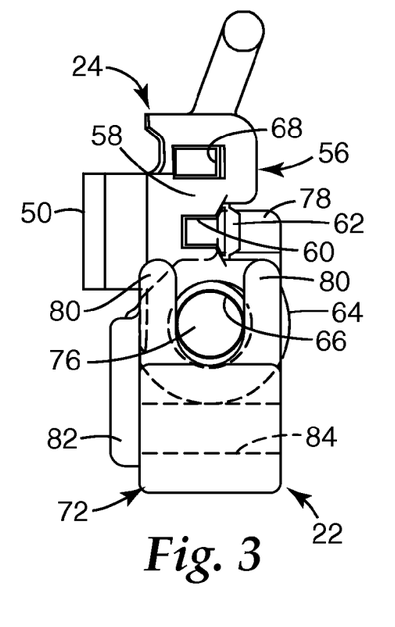
FIG. 3 is a side elevational view of the attachment module and buccal tube appliance shown in FIG. 2, looking in a mesial direction.
Figure 4:
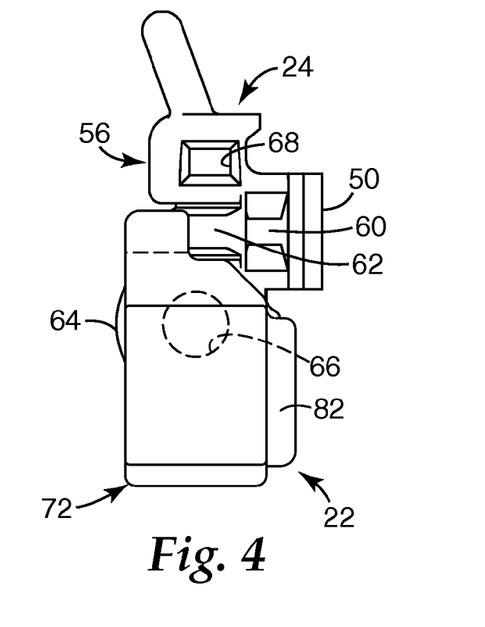
FIG. 4 is a view somewhat similar to FIG. 3 except looking at the attachment module and buccal tube appliance in a distal direction.

In the embodiment shown in the drawings, the inner surfaces of the second wall portions 64 have a generally cylindrical configuration and define the passage 66. Examples of suitable buccal tube appliances 24 include "double tube" molar appliances with a passage similar to passage 66 for optional reception of an orthodontic facebow or headgear component. Other examples of suitable buccal tube appliances include "triple tube" appliances that have, in addition to the passage and archwire slot of the "double tube" appliance, a third passage for another auxiliary component such as a wire arch segment. This auxiliary passage is optional and in FIGS. 2-4 is designated by the numeral 68. Examples of suitable commercially available buccal tube appliances include "Victory Series" brand triple convertible appliances from 3M Unitek Corporation.

Figure 5:
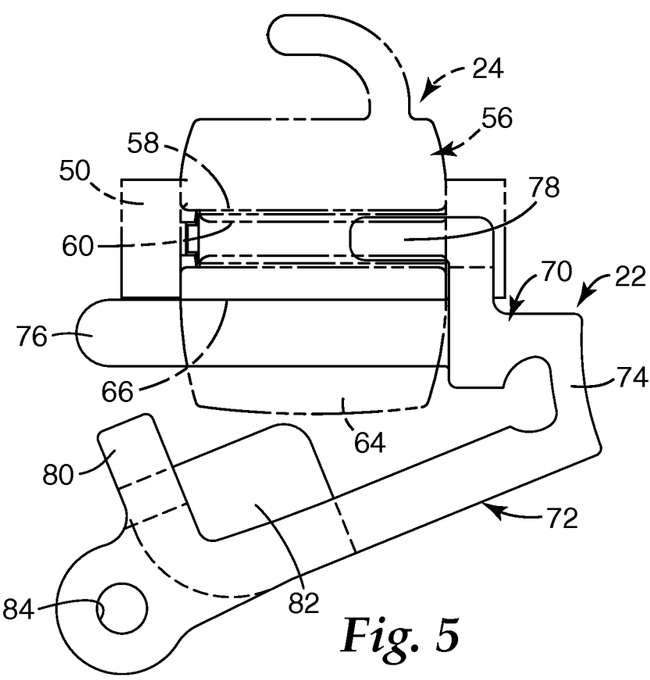
FIG. 5 is a view somewhat similar to FIG. 2 except showing the attachment module in an open orientation.
Figure 6:
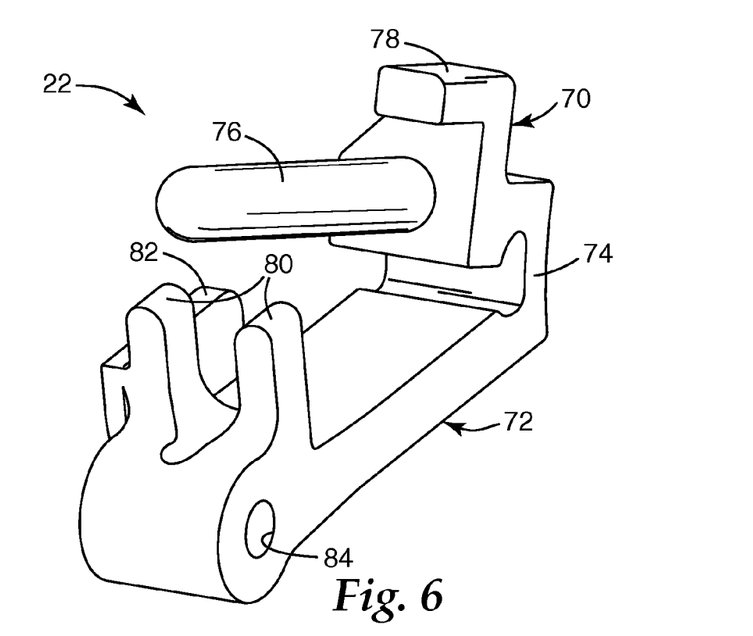
FIG. 6 is a perspective view of the attachment module alone that is illustrated in FIGS. 1-5, showing the attachment module in an open orientation.
Figure 7:
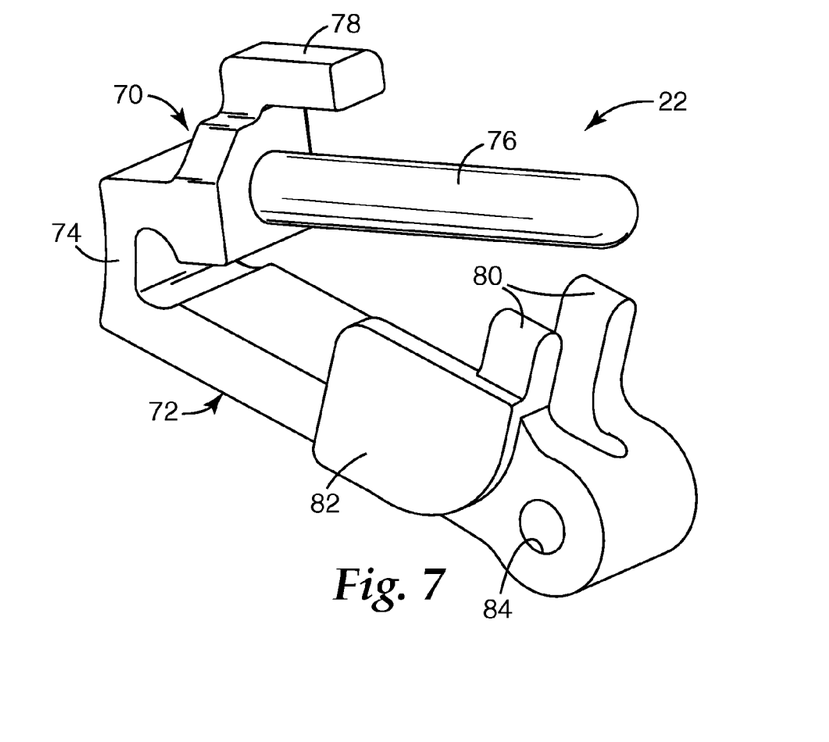
FIG. 7 is a perspective view somewhat similar to FIG. 6 except looking at the attachment module from a different viewpoint.

The attachment module 22 illustrated in FIGS. 1-7 is releasably coupled to the buccal tube appliance 24. The attachment module 22 includes a first segment 70 and a second segment 72 that is movably coupled to the first segment 70 by a hinge section 74. The hinge section 74 enables relative movement of the segments 70, 72 between an open orientation that is shown in FIGS. 5-7 and a closed orientation that is shown in FIGS. 1-4. The movement between the open and closed orientations in this embodiment represents a pivotal motion about a facial-lingual reference axis that is also perpendicular to the plane of the drawings of FIGS. 1, 2 and 5.

The first segment 70 includes an elongated shank 76 that preferably has a generally circular cross-sectional configuration that is complemental to the circular cross-sectional configuration of the passage 66. When the attachment module 22 is installed on the buccal tube appliance 24, the shank 76 extends through the passage 66 and preferably extends past the distal end of the passage 66 in a distal direction. Preferably, and as shown in the drawings, the outer or distal free end of the shank 76 is tapered to a rounded shape to facilitate reception of the shank 76 in the mesial opening of the mating passage 66 during installation of the attachment module 22.

The first segment 70 also includes a first rotation stop 78 that extends in generally parallel but spaced apart relation to the direction of extension of the shank 76. When the attachment module 22 is connected to the buccal tube appliance 24, the first rotation stop 78 is received in a location extending over the cap 62. In this embodiment, the rotation stop 78 is elongated but shorter in length than the overall length of the shank 76, although other constructions are also possible.

The second segment 72 includes two parallel, spaced apart pegs 80 that are remote from the hinge section 74. When the attachment module 22 is in its closed orientation, the pegs 80 straddle a distal section of the shank 76 and are located in a distal direction from the distal side of the buccal tube appliance 24. The pegs 80 help resist deformation of the attachment module 22 when unexpected forces are encountered, such as twisting movement of the second segment 72 relative to the first segment 70 in an arc about an occlusal-gingival reference axis.

The second segment 72 also includes a second rotation stop 82 that has a generally flat shape. The second rotation stop 82 is located in a lingual direction relative to the pegs 80, and is also located in a lingual direction relative to the shank 76 when the attachment module 22 is in its closed orientation. The second rotation stop 82 extends along the lingual side of the second wall portions 64 that define the passage 66 when the attachment module 22 is secured to the buccal tube appliance 24.

The second segment 72 also includes an outermost, distal end with a coupling that comprises a cylindrical opening 84 in this exemplary embodiment. The bite corrector 26 (FIG. 1) is pivotally connected to the attachment module 22 by a pin 86 that extends through the opening 84 as well as through a matching opening of the connector 48 of the bite corrector 26. The pin 86 has an enlarged, outer head to prevent detachment of the bite corrector 26 from the attachment module 22, and may be secured to the second segment 72 by any suitable means such as a laser weld, a resistance weld, an interference fit or the like.

Preferably, the attachment module 22 is supplied to the practitioner by the manufacturer in the open orientation that is shown in FIGS. 5-7, and preferably has been previously connected to the bite corrector 26 by the manufacturer. The practitioner installs the attachment module 22 by placing the distal, free end of the shank 76 in the mesial opening of the passage 66. The attachment module 22 is then moved in sliding fashion in a distal direction relative to the buccal tube appliance 24 until such time as the mesial side of the buccal tube appliance 24 engages the flange of the attachment module 22 that surrounds the mesial end of the shank 76. In this position of the attachment module 22, the outer, distal end section of the shank 76 extends past the distal side of the buccal tube appliance 24 in a distal direction.

Next, the attachment module 22 is pinched or squeezed to a closed orientation as shown in FIGS. 1-4. For example, the practitioner may use a hand instrument such as Weingart pliers or How pliers to pivot the second segment 72 relative to the first segment 70 and move the second segment 72 in an upward direction and along a curved path. When the attachment module 22 is in its closed orientation, the upper or gingival side of the second segment 72 is in contact with or closely adjacent the bottom or occlusal side of the buccal tube appliance 24 and the pegs 80 straddle the distal end section of the shank 76 on its lingual and facial sides.

As the attachment module 22 is moved from its open orientation to its closed orientation, the second rotation stop 82 moves upwardly in an arc and into a region between the lingual side of the second wall portions 64 and the adjacent surface of the molar tooth 54 (or adjacent the band 52 as the case may be, depending on the size and location of the adjacent portions of the band 52). Once the attachment module 22 is closed, the second rotation stop 82 limits bending or twisting movements of the second segment 72 in generally facial directions away from the molar tooth 54. In addition, the first rotation stop 78 serves to limit movement of the attachment module 22 and the bite corrector 26 in a counterclockwise arc viewing FIG. 3 about the longitudinal axis of the shank 76.

Advantageously, movement of the second segment 72 relative to the first segment 70 during installation of the attachment module 22 enables the rotation stop 82 to be placed into the relatively small region on the lingual side of the second wall portions 64 without undue difficulty. This advantage is especially beneficial since components such as the attachment module 22 and the buccal tube appliance 24 are relatively small and access to areas of the oral cavity adjacent the first molar teeth is limited. Moreover, the mesial portions of certain commercially available buccal tube appliances may have structure that precludes placement of the rotation stop 82 in the position shown in FIGS. 2-4 by approaching this position from the mesial side of the appliance.

The hinge section 74, and optionally the entire attachment module 22, is comprised of a highly malleable metallic material, such as 17-4 PH stainless steel. Optionally, the hinge section 74 has a lower temper than remaining portions of the attachment module 22. Preferably, the attachment module 22 is integral and fabricated as a single component. Optionally, the attachment module 22 is manufactured using a metal injection molding process.

Although not shown in the drawings, an assembly somewhat similar to assembly 20 may be affixed to orthodontic components on the left side of the patient's jaws. In addition, other types of bite correctors or force modules and buccal tube appliances may be used in place of the bite corrector 26 and buccal tube appliance 24 illustrated in the drawings.

Figure 8:
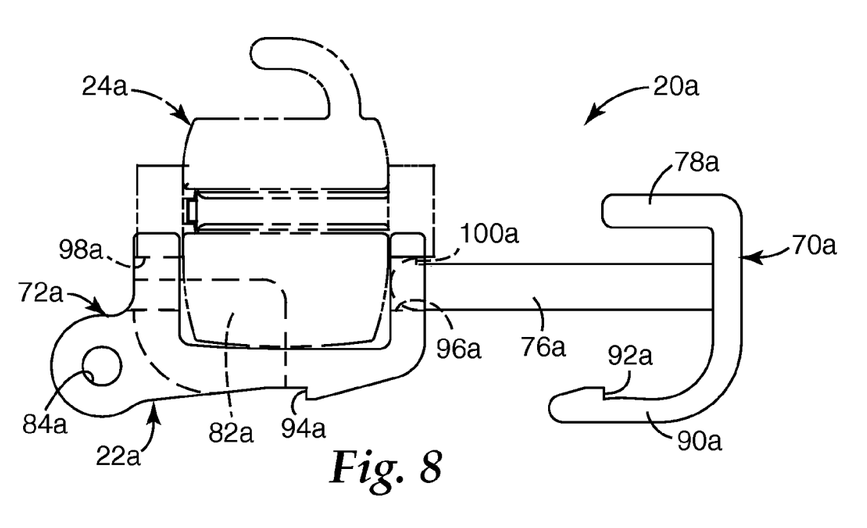
FIG. 8 is a front elevational view of an attachment module according to another embodiment of the present invention along with an orthodontic buccal tube appliance, illustrating the attachment module in an open orientation.
Figure 9:
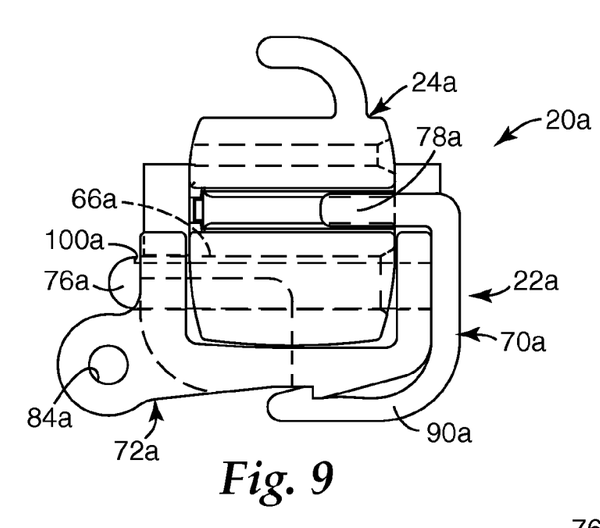
FIG. 9 is a view somewhat similar to FIG. 8 except depicting the attachment module in a closed orientation.
Figure 10:
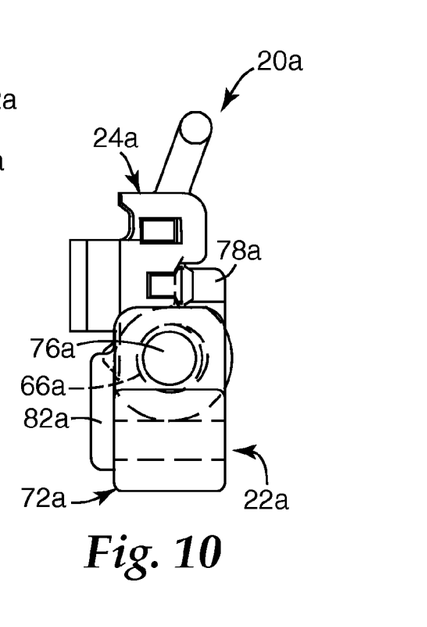
FIG. 10 is a side elevational view of the attachment module and buccal tube appliance illustrated in FIGS. 8 and 9, looking in a mesial direction.

An orthodontic assembly 20a according to another embodiment of the invention is illustrated in FIGS. 8-10. The assembly 20a includes a buccal tube appliance 24a and a bite corrector (not shown in FIGS. 8-10). The buccal tube appliance 24a and the bite corrector of the assembly 20a are similar to the buccal tube appliance 24 and the bite corrector 26 described above, and as such a detailed description of such components need not be repeated.

The orthodontic assembly 20a also includes an attachment module 22a releasably coupled to the buccal tube appliance 24a. The attachment module 22a includes a first segment 70a that comprises an elongated shank 76a and a first rotation stop 78a. The shank 76a and the rotation stop 78a extend in generally parallel directions along a mesial-distal reference axis when the attachment module 22a is connected to the buccal tube appliance 24a.

The first segment 70a also includes a curved arm 90a that first extends in an occlusal direction away from the mesial end of the shank 76a and then extends in a distal direction. An outer end of the arm 90a includes a shoulder 92a. The distal end of the shank 76a also includes a shoulder 100a.

The attachment module 22a also includes a generally "U"-shaped second segment 72a having a mesial aperture 96a and a distal aperture 98a on opposite ends. The mesial aperture 96a includes a restriction such as a flange or shoulder (not shown) that contacts the shoulder 100a as the first segment 70a is moved in a mesial direction relative to the second segment 72a. As a consequence, the first segment 70a cannot detach from the second segment 72a in ordinary use. The center, occlusal portion of the second segment 72a includes a shoulder 94a (see, e.g., FIG. 8).

The attachment module 22a includes a second rotation stop 82a that extends along the distal and lingual portions of the second segment 72a. The second rotation stop 82a is releasably received in a region located in a lingual direction from wall portions of the buccal tube appliance 24a adjacent the passage, similar to the position of the second rotation stop 82 relative to the second wall portions 64 described in connection with the embodiment shown in FIGS. 1-7. The second segment 72a also includes an opening 84a for connection to the bite corrector.

To install the attachment module 22a and secure the attachment module 22a to the buccal tube appliance 24a, the attachment module 22a is initially in its open orientation as depicted in FIG. 8. If not previously provided, this open orientation is attained by movement of the first segment 70a in directions away from the second segment 72a, preferably until the limit of such movement is reached due to contact of the shoulder 100a with the restriction provided in the mesial aperture 96a. Next, the second segment 72a is placed along the occlusal side of the buccal tube attachment 24a and moved in a gingival direction. Continued movement of the attachment module 22a in a gingival direction brings the second rotation stop 82a to a position next to the lingual side of the wall portions defining the passage of the buccal tube appliance 24a and also moves the center portion of the second segment 72a proximal to the occlusal side of the buccal tube appliance 24a. In this position of the second segment 72a, the apertures 96a, 98a are in alignment with the central axis of the passage 66a.

Next, the first segment 70a is moved relative to the second segment 72a and in a distal direction in order to move the shank 76a through the mesial aperture 96a and into the passage 66a. Movement of the first segment 70a in a distal direction is continued until the shoulder 92a latches with shoulder 94a. The attachment module 22a is then its closed orientation as shown in FIG. 9.

When the attachment module 22a is in its closed orientation, the first rotation stop 78a extends over the cap of the buccal tube appliance 24a. In addition, the latching provided by the engagement of the shoulders 92a, 94a prevents inadvertent movement of the first segment 70a in a mesial direction relative to the second segment 72a. As a consequence, the attachment module 22a is securely connected to the buccal tube appliance 24a until such time as the practitioner decides to move the attachment module 22a to its open orientation. To open the attachment module 22a, the arm 90a is moved in an occlusal direction with a hand instrument until such time as the shoulders 92a, 94a disengage each other. The first segment 70a is then shifted in a mesial direction.

Figure 11:
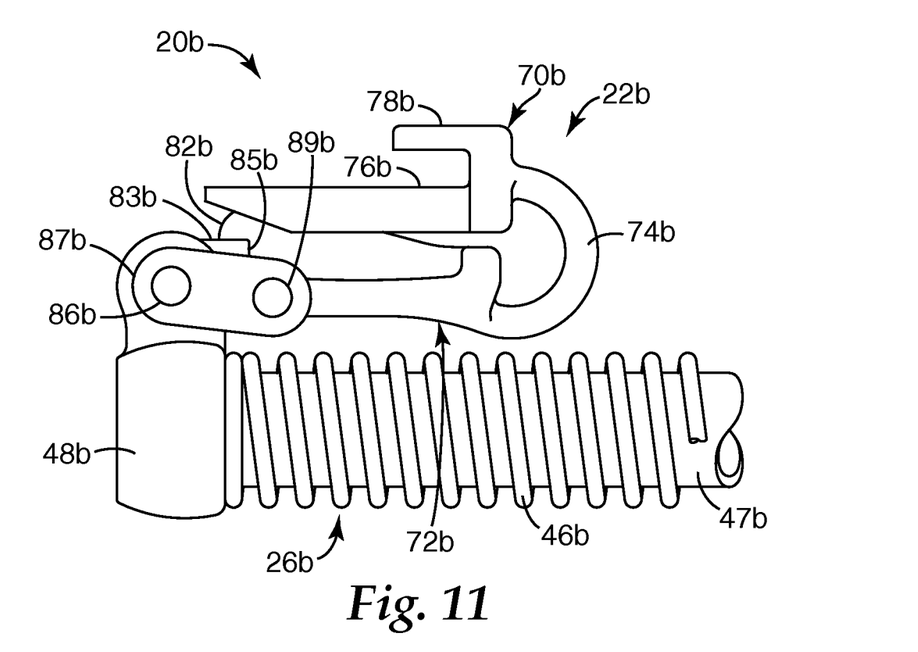
FIG. 11 is a front elevational view of an attachment module according to still another embodiment of the present invention along with a portion of a bite corrector.
Figure 12:
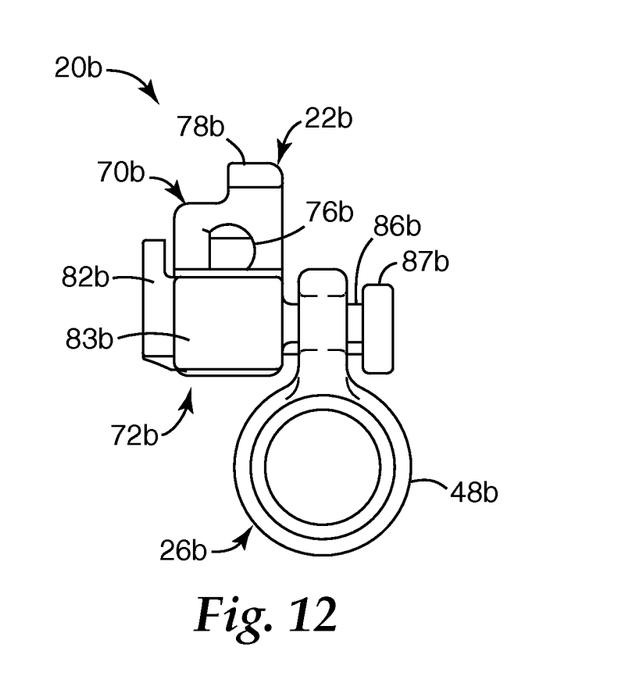
FIG. 12 is side elevational view of the attachment module and bite corrector shown in FIG. 11, looking at the attachment module and bite corrector in a mesial direction.

An orthodontic assembly 20b according to a further embodiment of the invention is illustrated in FIGS. 11 and 12. The assembly 20b includes an attachment module 22b and a bite corrector 26b. The assembly 20b also includes a buccal tube appliance that is not shown in FIGS. 11 and 12, but is optionally similar or identical to the buccal tube appliances 24, 24a depicted in FIGS. 1-5 and 8-10.

The attachment module 22b includes a first segment 70b that comprises an elongated shank 76b and a first rotation stop 78b that is spaced from the shank 76b. The shank 76b and the rotation stop 78b extend in generally parallel directions along a mesial-distal reference axis when the attachment module 22b is connected to a buccal tube appliance.

The attachment module 22b also includes a second segment 72b with a second rotation stop 82b. The distal end of the second segment 72b terminates in a body 83b that presents a shoulder 85b. A post 86b extends outwardly from the body 83b in a facial direction. A second post 89b extends in generally parallel relation to the post 86b and is connected to the second segment 72b at a location adjacent the shoulder 85b. Preferably, the posts 86b, 89b are integrally molded as part of the second segment 72b.

A third segment 74b of the attachment module 22b has a generally "C"-shaped configuration and integrally connects the first segment 70b to the second segment 72b. The third segment 74b is sufficiently resilient to enable movement of the second segment 72b relative to the first segment 70b in directions toward and away from each other. Preferably, the first segment 70b and the second segment 72b are oriented as shown in FIGS. 11 and 12 when the third portion 74b is in its normal, relaxed condition.

The attachment module 22b is connected to a buccal tube appliance such as the appliance 24 shown in FIGS. 1-5 by placing the distal free end of the shank 76b in the mesial opening of a passage in the buccal tube appliance, such as the passage that is otherwise often used to receive an orthodontic facebow or headgear component. The outer or distal free end of the shank 76b is tapered as shown in the drawings to facilitate reception of the shank 76b in the passage of the buccal tube appliance.

As the orthodontic practitioner urges the attachment module 22b against the buccal tube appliance in a distal direction, the first and second segments 70b, 72b self-move away from each other a distance sufficient to enlarge the space between the outer end of the shank 76b and the shoulder 85b of the body 83b. Such movement is enabled by the inherent resilience of the third segment 74b and preferably can be carried out by finger pressure against the module 22b without the use of hand instruments or the like.

As the attachment module 22b continues to move in a distal direction relative to the buccal tube appliance, the outer end of the shank 85b emerges from the distal side of the passage of the buccal tube appliance. Continued movement of the attachment module 22b in a distal direction enables the shoulder 85b to be located on the distal side of the buccal tube appliance. Once the shoulder 85b has cleared the buccal tube appliance in this manner, the inherent resilience of the third segment 74b causes the first and second segments 70b, 72b to relatively move toward each other and toward their closed, relaxed orientations as shown in FIGS. 11 and 12.

The resilience of the third segment 74b, in combination with the shape of the second segment 72b including the shoulder 85b, enables the buccal tube appliance to "snap-fit" into its position located on the mesial side of the shoulder 85b such that the attachment module 22b is held captive in place. This "snap-fit" relationship is similar to the "snap-fit" relationship described in connection with the orthodontic coupling described in the aforementioned U.S. Pat. No. 6,913,460. During treatment, the inherent resilience of the third segment 74b helps to ensure that the attachment module 22b remains connected to the buccal tube appliance until such time as the practitioner desires to release the attachment module 22b from the buccal tube appliance. In practice, the attachment module 22b may be released when desired by pressing on the attachment module 22b or the bite corrector 26b in an occlusal direction (i.e., in a downwardly direction viewing the arrangement shown in FIG. 11) in order to widen the space between the shank 76b and the shoulder 85b so that the attachment module 22b can then be moved in a mesial direction for disengagement from the buccal tube appliance.

When the attachment module 22b is connected to the buccal tube appliance, the first rotation stop 78b extends over a facial portion of the buccal tube appliance, such as a facial side of a removable cap similar to the archwire slot cap 62 described above. The first rotation stop 78b serves to limit movement of the attachment module 22b and the bite corrector 26b in a counterclockwise arc viewing FIG. 12 about the longitudinal axis of the shank 76b.

Additionally, when the attachment module 22b is connected to the buccal tube appliance, the second rotation stop 82b extends along a lingual portion of the buccal tube appliance, similar to the orientation of the second rotation stop 82 relative to the buccal tube appliance 24 as shown in FIGS. 2-4. The second rotation stop 82b limits bending or twisting movements of the second segment 72b in generally facial directions away from the adjacent tooth. As can be appreciated by reference to FIGS. 11 and 12, the first rotation stop 78b is spaced from the shank 76b in a direction along a first reference axis and extends in a direction generally parallel to the shank 76b, while the second rotation stop 82b is spaced from the shank 76b in a direction along a second reference axis that is generally perpendicular to the first reference axis.

The bite corrector 26b is optionally similar to the bite corrector 26 described above and includes a first elongated tubular member 47b that is shown in FIG. 11. A helical compression spring 46b extends around the first tubular member 47b and has an outer end that bears against a connector 48b of the bite corrector 26b that is fixed to the first member 47b.

The connector 48b of the bite corrector 26b includes a tab with a circular opening that is received on the post 86b of the second segment 72b. A flat, oval-shaped cap 87b is welded to the outer ends of the posts 86b, 89b and serves to secure the bite corrector 26b in a pivotally connected relationship to the attachment module 22b. Advantageously, the flat facial side of the plate 87b is relatively broad and reduces the risk of patient discomfort if contact is made with adjacent oral tissue of the patient. Moreover, the two integrally molded posts 86b, 89b serve to securely connect the bite corrector 26*b* to the attachment module 22*b* through a stronger structure than may be provided by a ball pin or the like.

Other aspects of the assembly 20*b* including the attachment module 22*b* are similar to the various aspects of the assemblies 20, 20*a* including the attachment modules 22, 22*a* described above.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. An orthodontic attachment module for an orthodontic bite corrector comprising:
    a first segment including a first body and an elongated shank for reception into a passage of an orthodontic buccal tube appliance, the first segment also including a first rotation stop separate and spaced from the shank in a direction along a first reference axis, wherein the first rotation stop is a post that extends from the body to a free end, the post extending in parallel to the shank;
    a second segment including a coupling for connection to an orthodontic bite corrector, wherein the second segment is movable relative to the first segment between an open orientation and a closed orientation; and
    a third segment that interconnects the first segment and the second segment, wherein the third segment enables movement of the second segment relative to the first segment in directions toward and away from each other.

2. An orthodontic attachment module according to claim 1, wherein the third segment enables pivotal movement of the second segment relative to the first segment.

3. An orthodontic attachment module according to claim 1, wherein the third segment is resilient.

4. An orthodontic attachment module according to claim 1, wherein the second segment includes a generally flat surface that acts as a second rotation stop and includes portions extending parallel to the first reference axis, the flat surface spaced from the shank in a direction along a second reference axis that is generally perpendicular to the first reference axis.

5. An orthodontic attachment module according to claim 1, wherein the third segment exhibits a generally C-shaped configuration.

6. An orthodontic attachment module according to claim 1, and wherein the first reference axis is an occlusal-gingival axis.

7. An orthodontic attachment module according to claim 1, wherein the second segment includes a pair of spaced apart pegs that straddle and receive a free end of the shank when the attachment module is in its closed orientation.

8. An orthodontic attachment module according to claim 1, wherein an end of the second segment terminates in a shoulder.

9. The attachment module according to claim 1, wherein the second segment includes a flat surface that acts as a second rotation stop, and wherein the flat surface is located in a generally lingual direction from the shoulder.

10. An orthodontic assembly comprising:
    a buccal tube appliance including a base for bonding to a tooth surface and a body extending outwardly from the base, the body including first wall portions defining an archwire slot extending in a mesial-distal direction and second wall portions defining a passage extending in a generally mesial-distal direction; and
    an attachment module releasably connected to the buccal tube appliance, the attachment module including a shank extending into the passage and a post acting as a first rotation stop extending over the buccal tube body and located in a facial direction relative to at least a portion of the body, the attachment module also including a generally flat surface that acts as a second rotation stop that is movable relative to the first rotation stop, wherein the attachment module includes a first segment that comprises the first rotation stop, a second segment that comprises the second rotation stop and a section that integrally interconnects the first segment and the second segment and enables the relative movement of the segments between an open state and a closed state, and wherein, in the closed state, the flat surface is located outside the passage in a lingual direction relative to the shank and the flat surface extends along a portion of the body between the passage and the tooth surface.

11. The orthodontic assembly of claim 10, wherein the shank and the first rotation stop extend in generally parallel directions along a mesial-distal reference axis.

12. An orthodontic assembly according to claim 10 wherein the second rotation stop is pivotally movable relative to the first rotation stop.

13. An orthodontic assembly according to claim 10, wherein the section comprises a resilient third segment.

14. An orthodontic assembly according to claim 13, wherein the resilient third segment enables movement of the second segment relative to the first segment in directions toward and away from each other.

15. An orthodontic assembly according to claim 13, wherein the third segment exhibits a generally C-shaped configuration.

16. An orthodontic assembly according to claim 10, and wherein the post is located in a generally occlusal-gingival direction from the shank.

17. An orthodontic assembly according to claim 10 and further comprising a bite corrector coupled to the second segment.

18. An orthodontic assembly according to claim 10, wherein an end of the second segment terminates in a body that includes a shoulder.

19. An orthodontic assembly according to claim 18, wherein the flat surface is located in a generally lingual direction from the shoulder.

20. An orthodontic assembly according to claim 10 wherein the second rotation stop is movable relative to the first rotation stop in directions along a facial-lingual axis.

21. A method of coupling an orthodontic attachment module to an orthodontic buccal tube appliance comprising:
    providing a buccal tube appliance having first wall portions defining an elongated archwire slot and second wall portions defining an elongated passage extending alongside the archwire slot;
    placing a shank of an attachment module in the passage, the attachment module further including,
    a first rotation stop separate and spaced from the shank in a direction along a first reference axis, wherein the first rotation stop extends to a free end in a direction generally parallel to the shank, and
    a second rotation stop spaced from the shank in a direction along a second reference axis that is generally perpendicular to the first reference axis; and moving the second rotation stop relative to the first rotation stop and into a region that is located in a lingual direction relative to the second wall portions, and wherein the act of moving the rotation stop into the region is carried out at a time other than during the act of placing the shank in the passage.

* * * * *